United States Patent [19]

Roland

[11] Patent Number: 4,585,738

[45] Date of Patent: Apr. 29, 1986

[54] IMMOBILIZED ENZYME SYSTEMS

[75] Inventor: John F. Roland, Glenview, Ill.

[73] Assignee: Kraft, Inc., Glenview, Ill.

[21] Appl. No.: 529,019

[22] Filed: Sep. 2, 1983

[51] Int. Cl.$^4$ .................. C12N 11/14; C12N 11/02; C12N 11/12; C12N 11/08

[52] U.S. Cl. .................................... 435/176; 426/31; 426/41; 426/42; 435/177; 435/179; 435/180; 435/181; 435/188

[58] Field of Search ............... 435/176, 177, 179, 180, 435/181, 188; 426/34, 41, 42

[56] References Cited

U.S. PATENT DOCUMENTS 3,852,496  12/1974  Weetall et al. .................. 426/41
4,090,919   5/1978  Chibata et al. ................. 435/178

OTHER PUBLICATIONS

Wheeler, "Science", v. 204 (1979), pp. 6 and 8.
Millin et al., "Process Biochemistry", (Jun., 1967), pp. 9–13.
Roberts et al., "J. Sci. Food Agric.", 9, (Nov. 1958), pp. 701–705.
Kumar et al., "Agric. Food Chem." 32, (1984), pp. 447–453.
Roland, "Enzyme Microb. Technol." v. 3, (Apr. 1981), pp. 105–110.
*Merck Index*, 9th Ed., pp. 1172–1173.
Haslam, *Chemistry of Vegetable Tannins*, (1966), Academic Press, N.Y., pp. 14–17, 68–121.
*Immobilized Enzymes for Food Processing*, Pitcher (ed.), (1980), CRC Press, Fla., pp. 55–80.

*Primary Examiner*—Robert J. Warden
*Assistant Examiner*—P. Kate White
*Attorney, Agent, or Firm*—Fitch, Even, Tabin & Flannery

[57] ABSTRACT

Immobilized enzyme systems which contain a tea polyphenol-enzyme adduct and the methods for preparing and using such immobilized enzyme systems.

10 Claims, No Drawings

IMMOBILIZED ENZYME SYSTEMS

BACKGROUND OF THE INVENTION

The present invention is directed to processes for preparing enzymes as well as the immobilized enzyme compositions themselves, and methods for processing liquid substrates, particularly food products, by means of such immobilized enzyme compositions.

Enzymes produced by cells of plants, animals and microorganisms have long been used in food and other industrial processing for their catalytic effect.

Substantial effort has been directed to the preparation of immobilized enzyme systems, in which enzymes are converted from a water-soluble mobile state to an immobile state to improve process control and facilitate separation of the enzyme from the reactant while retaining, at least in part, their capacity for interaction with specific substrates [Kilbanov, A.M., Science, 219, 722, (1983); O. R. Zaborsky, Immobilized Enzymes, CRC Press, Cleveland, Ohio (1973), G. P. Royer, Catal. Rev. Sci. Eng. 22 (1) 29–73 (1980); J. F. Roland, "Requirements Unique to the Food and Beverage Industry", *Immobilized Enzymes for Food Processing*, Ed. W. H. Pitcher, CRC Press, Boca Raton, Fla. (1980)].

Food processors have had a long and continuing interest in developing the potential of enzyme systems to modify foods and beverages. In recent years, this interest has been intensified by the development of immobilization procedures that allow enzymes to be attached to solid surfaces while still retaining their functionality. Enzyme immobilization permits a high degree of process control, and reuse of the enzyme over an expanded time period. Because the enzyme no longer appears as an additive in the final product, an additional processing step to remove it in order to prevent overtreatment during storage due to continuing activity is not necessary. Major industrial-scale immobilized enzyme processes in which various amino acylases adsorbed to DEAE cellulose or DEAE agarose are employed to convert tonnage quantities of synthetic DL amino acids to the biologically available L-form. Similarly, glucose isomerase adsorbed to DEAE cellulose has been used in the full-scale conversion of corn syrup sugar to fructose.

However, there are problems arising in the utilization of immmobilized enzymes in food and beverage processing. It is, of course, not only essential that the immobilization treatment preserve enzyme activity, but it is also essential that the components of the immobilized enzyme composition and the degraded enzyme be safe for use in food products. The health and safety aspects of employing enzymes in food processing have been discussed in Enzyme Microb. Technol. 3, 105 (1981).

Enzymes have conventionally been immobilized by various methods including covalent attachment, adsorption, entrapment, crosslinking and encapsulation.

Tannic acid has been used, together with glyceraldehyde for enzyme immoblization, as described in U.S. Pat. No. 3,736,231, but its use may be restricted from food applications due to the known toxic effects of tannin in humans.

For example, U.S. Pat. No. 4,113,567 describes a modified phenolic polymer substrate for enzyme immobilization, in which the phenolic polymer has pendant aldehyde or diazonium salt groups. U.S. Pat. No. 3,767,531 concerns immobilization of an active enzyme by glutaraldehyde on a substrate of phenol formaldehyde resin. U.S. Pat. Nos. 3,992,329 and 4,078,970 relate to adsorption of an enzyme such as glucose isomerase within the pores of an inorganic support, or a porous anion exchange resin. U.S. Pat. Nos. 3,852,496 and 4,016,293 concern a process for using insolubilized lactase to hydrolyze lactose from cheese whey, in which the enzyme is treated with glutaraldehyde, silane coupling agents or other materials. U.S. Pat. No. 4,338,398 describes the cross-linking of starch degrading enzymes with a wide variety of mono and polyfunctional materials such as aldehydes, isocyanates and methylol groups, and their absorption onto a water insoluble, porous substrate.

As indicated, in order to carry out these immoblization procedures, a wide variety of chemical agents, insoluble supports and solvents have been employed, but most have substantial disadvantages for use in systems intended for food processing utilization. For example, these systems which rely on cyano- or halogenated chemical derivatives, aldehydes, isocyanates, carbodiamides, diazo compounds, phosgene derivatives and the like for enzyme attachment, spacing or cross liking are undesirable for use in food processing because of the toxic potentials of these compounds. The use of glutaraldehyde as an effective cross-linking agent for enzymes has been recognized for many years. However, commercial solutions may contain undesirable quantities of substances such as acrolein, glutaric acid and glutaraldoxine and the continuing development of biological data in respect to glutaraldehyde may indicate undesirable properties for food processing use. It is apparent that the presence of these agents in enzyme modified foodstuffs, due to degradation, would constitute a serious health hazard. Therefore, it is important to find systems for immobilizing enzymes in which all of the components are recognized as safe and are also inexpensive.

Accordingly, it is an object of the present invention to provide processes for preparing insolublized enzyme compositions which utilize food grade materials which are generally recognized as safe for human consumption. It is a further object to provide active immobilized enzyme compositions prepared from edible components and having extended useful life for enzymatic processing. An additional object is the provision of enzymatic food processing processes utilizing such compositions.

DESCRIPTION OF THE INVENTION

Generally, the present invention is directed to processes for preparing immobilized enzyme compositions as well as the immobilized enzyme compositions themselves. Moreover, various aspects of the present invention are directed to methods for enzymatic processing of liquid substrates, particularly including food product substrates, by means of such immobilized enzyme compositions.

In accordance with the present disclosure, methods for preparing immobilized enzyme compositions generally comprise the steps of providing an enzyme composition to be immobilized, providing an insoluble support for the enzyme, and combining the enzyme and the insoluble support with a tea polyphenol immobilization agent to form an immobilized enzymatically active composition comprising an adduct of the enzyme, the substrate and the tea polyphenol immobilization agent. As will be described in more detail hereinafter, tea polyphenol immobilization agents which are important aspects of the method and compositions described herein, may be obtained from the water soluble components of green or fermented tea, as a food-safe immobilization agent. Preferred embodiments of such preparation processes include the steps of forming a solution of the tea polyphenol immobilization agent, which is preferably an aqueous solution, admixing the immobilization support with the tea polyphenol solution to form a tea polyphenol-support adduct, preparing an aqueous solution of the enzyme to be immobilized, and admixing the tea polyphenol-support adduct with the aqueous enzyme solution to provide a tea polyphenol-support enzyme adduct. Desirably, the admixing of the enzyme with the insoluble support component may be carried out at a pH which is at or near (e.g., ± one pH unit) the isoelectric point of the enzyme. The tea polyphenol immobilization agent may also be admixed with the aqueous enzyme solution to form a tea polyphenol-enzyme adduct, which may subsequently be admixed with the selected support, if desired. Similarly, the tea polyphenol immobilization agent, the insoluble support and the enzyme may be simultaneously admixed in a suitable aqueous vehicle.

As also discussed, a suitable insoluble support for immobilization of the enzyme is also provided. In this regard, insoluble enzyme support substrates are well known in the art.

In accordance with various aspects of the present invention, enzymes may be immobilized on either organic or inorganic substrates in accordance with a variety of known immobilization techniques and procedures which further include the utilization of a tea polyphenol immobilization agent. In accordance with one type of immobilization technique, the enzyme may be adsorbed onto a charged surface, such as an ion-exchange resin. Particularly preferred are organopolymeric enzyme supports which have pendant anionic and/or cationic groups, particularly including carboxylic acid groups and/or amino groups to provide for enhanced enzyme adsorption to the support. However, enzymes insolublized in this manner without the tea polyphenol immobilization agent may slowly leach back into solution, as will be described in more detail hereinafter. Enzyme molecules may also be covalently bonded to the surface of chemically reactive support materials, or entrapped in the interstices of an organic or inorganic polymer structure in accordance with conventional practice, and further immoblized by means of a tea polyphenol immobilization agent.

Particulate, rigid, inorganic support materials may, for example, desirably be utilized in low to moderate enzyme loading compositions. Such supports have excellent flow properties and when used in a packed bed may generally be used at higher flow rate than immobilized enzyme compositions prepared with organopolymeric support materials, by virtue of higher density of the inorganic support component. Organopolymeric support materials, on the other hand, may be provided with a variety of functional groups and may typically be utilized for higher enzyme loading, thereby providing a higher space density of the active enzyme component of the immobilized enzyme system. Composite organic-inorganic support particles may also be used.

The support may also be selected to provide a more hydrophobic or differently charged microenvironment than the enzyme molecule would encounter in free aqueous solution.

The immobilized enzyme product and the method of immobilization may be selected to complement the particular reactor design contemplated. In this regard, reaction apparatus may be of the tank-reactor type, or the column-reactor type. Tank reactors may be batch reactors in which the immobilized enzyme composition is mixed with the reactant solution until the product is formed; such tank reactors may be simple batch reactors or continuously stirred tank reactors, and may include a membrane or other filtration apparatus at the product steam outlet to maintain the insolubilized enzyme composition within the reactor. The reactor may also be a column-type reactor such as a packed bed reactor in which the immobilized enzyme is packed in a cylinder through which reactant solution is pumped, or a fluidized bed reactor in which the immobilized enzyme is placed loosely in a column and the reactant stream flow adjusted to cause the particles of immobilized enzyme to be levitated and thoroughly mixed in the reactant stream. The support materials may desirably be in bead form.

Examples of conventional support materials include carboxymethyl cellulose, alumino-silicates (molecular sieves), glass/cellulose composites, ceramics, phenolic-hydroxyl resins and ion exchange resins such as polyanionic and polycationic resins generally recognized as safe for food processing such as various of the Duolite resins commercially available from Rohm & Haas (e.g., Duolite 761, Duolite A6 and Duolite A7 products of Rohm & Haas).

Various useful food processes include the manufacture of high fructose corn syrup by means of immobilized glucose isomerase which converts glucose to fructose until an equilibrium mixture is obtained, starch hydrolysis to glucose by means of immobilized glucoamylase, the hydrolysis of lactose to glucose and galactose by means of immobilized lactase. In this latter regard, the feed streams for such immobilized lactase component may comprise whey, whey permeate and milk permeate. In addition, immobilized lactase may be utilized to hydrolyze lactose in milk to reduce the effects of lactose intolerance. Other processes include modification of milkfat by immobilized esterases, and modification of proteinaceous foodstuffs by proteolytic enzymes such as rennins, pepsin and papain.

As indicated, the enzyme to be immobilized and a suitable substrate therefor are provided for contacting with a tea polyphenol immobilization agent. In this regard, useful enzymes will be selected depending upon the particular enzyme process for which the immobilized enzyme composition is to be utilized.

Enzymes may include oxidoreductases, which are active in biological oxidation and reduction (including not only the dehydrogenases and oxidases, but also peroxidases, hydroxylases and oxygenases); transferases which catalyze the transfer of carbon groups, aldehydic or ketonic residues, acyl, glucosyl, or alkyl groups, nitrogenous groups and phosporous, and sulfurous containing groups; hydrolases, including esterases, phosphatases, glycosidases, peptidases; lyases, which remove groups from their substrates by a mechanism other than hydrolysis, including decarboxylases, aldolases, and dehydratases; isomerases which include racemases, epimerases, cis-trans isomerases, intramolecular oxidoreductases and intermolecular transferases; and ligases, which catalyze the joining together of two molecules coupled with the breakdown of a pyrophosphate bond. The enzyme should best be a purified enzyme, most preferably and should be substantially free of undesired enzymatic activity in respect to the intended enzymatic substrate which is to be processed. In this regard, the enzyme should best have a purity of at least 50 percent by weight and preferably at least 95 percent by weight. When the enzymatic activities of two or more selected enzymes are desired concurrently for a specific processing application, the weight percentages of the selected enzymes may be combined.

As indicated, in accordance with the present invention, tea polyphenols are utilized in the immobilization of enzymes. The tea polyphenol immobilization agent may desirably be selected from the group consisting of green or black tea, tea flavanols, tea bisflavanols, tea flavanol oxidation polymers and mixtures thereof. Tea polyphenols are derived from natural sources, being present in the aqueous extract of leaves of the plant *Camellia sinensis* (also known as *Thea sinensis*) which has long served as a natural human beverage. There are two principal kinds of aqueous tea infusions. Green tea is prepared without so-called "fermentation" while black tea is prepared from "fermented" tea leaves. Partially fermented teas (e.g., oolong teas) are regarded herein to be "fermented" teas. Green tea shoots contain a substantial quantity of polyphenolic substances which are water soluble. Quantitatively, the most important water soluble components of green tea are polyphenols. The catechins (flavan-3-ols) are the major substances of this group, and may amount to about 25% of the dry weight of the leaf. A representative approximate composition of green tea shoots (assam variety) is shown in the following table:

| APPROXIMATE COMPOSITION OF GREEN TEA SHOOTS (ASSAM VARIETY) | |
| --- | --- |
| | Dry Weight (%) |
| Substances soluble in hot water | |
| Flavanols (—) epi-gallocatechin gallate | 9–13 |
| (—) epi-catechin gallate | 3–6 |
| (—) epi-gallocatechin | 3–6 |
| (—) epi-catechin | 1–3 |
| other flavanals | 1–2 |
| Flavonols and flavonol glycosides | 3–4 |
| Leucoanthocyanins | 2–3 |
| Acids and depsides | 5 |
| Total polyphenols | 30 |
| Caffeine | 3–4 |
| Amino-acids | 4 |
| Simple carbohydrates | 4 |
| Organic Acids | 0.5 |
| Substances partially soluble in hot water | |
| Polysaccharides - Starch | 1–2 |
| Pectic substances, pentosans, etc. | 12 |
| Proteins | 15 |
| Ash | 5 |
| Substances insoluble in water | |
| Cellulose | 7 |
| Lignin | 6 |
| Lipids | 3 |
| Pigments | 0.5 |
| Volatile Substances | 0.01–0.02 |

Examples of specific tea polyphenols are as follows:

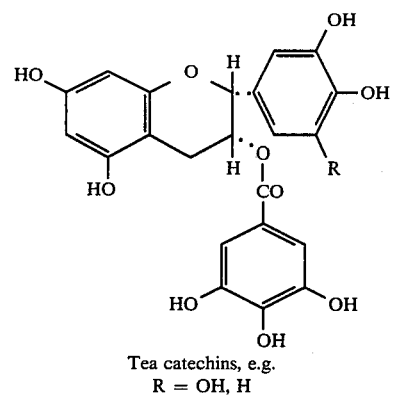

Tea catechins, e.g.
R = OH, H

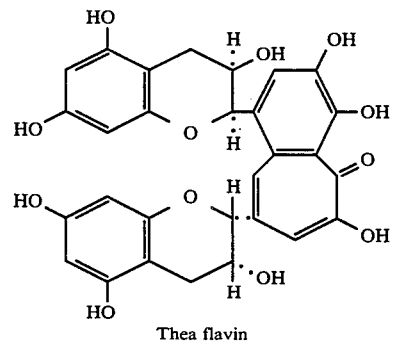

Thea flavin

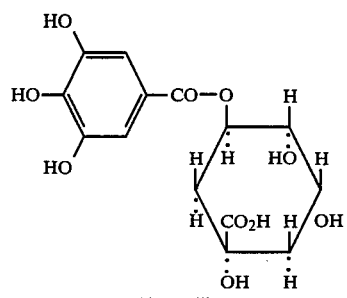

Theogallin

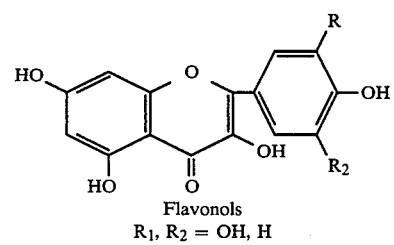

Flavonols
$R_1, R_2 = $ OH, H

Processing of the green tea leaf into black tea includes a so-called "fermentation" step which is primarily an enzymatic oxidation of tea polyphenols originally present in the green tea leaf. The term "fermentation" is accordingly a misnomer because it is an enzymatic oxidation apparently initiated by a polyphenol oxidase specific for the flavanols (catechins) and various other phenolic components of green tea leaf, but has acquired descriptive meaning with respect to tea processing and chemistry. During fermentation, the catechins are largely consumed to produce various more complex polyphenols including a series of ortho-quinones. For example, the following bisflavanols shown are believed to be included in the black tea oxidation product:

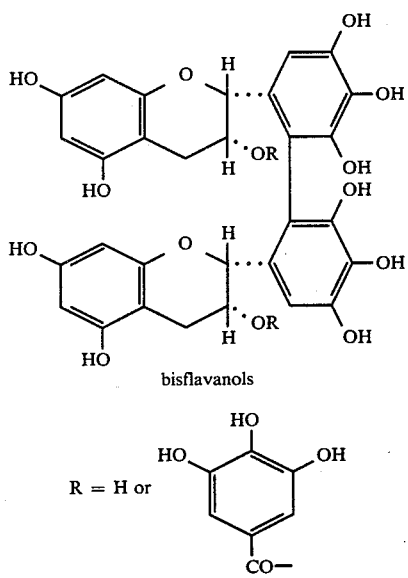

bisflavanols

R = H or [gallate ester structure]

The chemistry of tea polyphenols has been discussed by D. J. Millin, et al., "Nonvolatile Components of Black Tea and Their Contribution to the Character of the Beverage", J. Agric. & Food Chem., Vol. 17 (1969), pp. 717-721; E. A. H. Roberts, et al., "Theogallin, A Polyphenol Occurring in Tea", J. Sci. Food Agric., 9, pp 701-705 November, 1958; D. J. Millin, et al., "Tea Manufacture", Process Biochemistry, June, 1967, pp. 9-13; P. D. Collier, et al., "The Theaflavins of Black Tea", Tetrahedron, Vol. 29, pp. 125-142, 1973 (G. Britain); S. R. Wheeler, Science, 204, 6 (1979), which are incorporated herein by reference.

As indicated, the present invention is also directed to the immobilized enzyme compositions comprising a tea polyphenol enzyme adduct, and further to methods for processing food products utilizing such compositions. In this regard, such methods comprise the steps of providing an aqueous fluid dispersion (including solutions) of the food product to be processed which contains a reactant subject to enzymatic treatment, providing an insolublized enzyme composition comprising a tea polyphenol adduct of a selected enzyme for modifying the reactant, contacting the food product dispersion with the immobilized enzyme composition to enzymatically modify the food product, and separating the modified food product from the immobilized enzyme composition.

Preferred food and beverage processing methods include the treatment of dairy-derived lactose solutions with an immobilized tea polyphenol lactase enzyme composition and methods for manufacture of sugars such as invert sugar from starch or other carbohydrate material through the use of amylases and/or invertases or isomerases.

The components of one exemplary system involve the use of the enzyme beta-d-galactosidase (lactase) derived from the fermentation broth of *Aspergillis niger*. A commerical source used in these studies was Lactase LP, Wallerstein Co., Morton Grove, Ill. The enzyme has been recognized for many years as GRAS by the U.S. Food and Drug Administration.

The second component is a chemically modified cellulose prepared commercially in various forms such as gums or cellulose powders. These modified derivatives are carboxy cellulose compounds (CM-C) and again are utilized in food process and have GRAS status with the FDA.

The tea polyphenol component serves as an enzyme stabilizing agent, and may be applied either before or after the enzyme (lactase) has been adsorbed to the carboxy cellulose particles. Without the crosslinking effect provided by the tea polyphenol stablizing agent, the adsorption bond between the carboxymethyl cellulose and the active lactase enzyme is relatively weak and the active enzyme may be readily displaced by salts, etc., with a subsequent loss in activity.

In this instance, water soluble tea polyphenols present in tea are utilized as the crosslinking agent. The chemistry of tea is complex and has been reviewed by [D. J. Millen & R. W. Rustidge, Tea Manufacture, Process Biochemistry, June 1967, pp. 9-13]. A further understanding of the components present in black tea is [D. J. Millen, D. J. Crispen & D. Swaine, J. Agr. & Food Chem, 17, 717 (1969)]. Further it is reported [S. R. Wheeler, Sci. 204, 6 (1979)]that tea does not contain tannic acid (a hydrolyzable tannin that yields a hydrolysis, gallic acid and glucose).

The utilization of tea polyphenols including tea flavanols, comprising epi-gallocatechin gallate, epi-catechin gallate, epi-gallocatechin, and epi-catechin and polymeric oxidation products thereof to stabilize an absorbed enzyme complex and provide enhanced and prolonged functionality over an untreated system is further described with respect to the preparation and utilization of a tea polyphenol lactase carboxymethyl cellulose adduct.

In this regard, lactase (EC 3.2.1.23) may be adsorbed to carboxylated cellulose particles at an optimal pH, in accordance with conventional practices. However, the enzyme may be more firmly attached to the cellulose particles by soaking the cellulose in a cold solution of tea extract rich in tea polyphenols. After an appropriate soaking interval (e.g., 5 minutes to 24 hours), the enzyme is added and the insoluble crosslinked enzyme complex may be filtered. The excess tea polyphenol solution may be discarded. The bound enzyme may then be washed with an appropriate buffer, e.g., 0.05M acetate, pH 4.1 until the insoluble complex is free of tea components and unadsorbed enzyme.

A process for adsorption binding of the purified lactase enzyme to CM-cellulose at an optimal pH designed to provide the maximal loading of enzyme per gram of insoluble support is described in Example I.

EXAMPLE I

Beta galactosidase (lactase) originating from *A. niger* (lactase LP, Wallerstern Co., Morton Grove, Ill.) was used in a series of adsorption-binding experiments. The enzyme powder (700 mg) was dissolved in 4 separate containers containing 88 ml of 0.05M acetate buffer each adjusted to pH 3.0, 3.5, 4.0 and 4.5. The dissolved enzyme solutions contained a protein level of 1.006 milligrams per milliliter.

A commercial source of carboxymethyl cellulose particles (Vistec C.1) Koch-Light Laboratories, Ltd., Colnbrook Bucks, England, was used as the insoluble cation exchanger. The carboxymethyl cellulose media was precycled by soaking in 15 volumes of 0.5 molar aqueous sodium hydroxide solution for 30 minutes, followed by washing with deionized water and soaking in 0.5 molar aqueous hydrochloride acid for 30 minutes.

The cellulose media was then washed thoroughly with distilled water until the washings were neutral.

Twelve grams of the wet cellulose media were then added to each of the lactase solutions and again stabilized to pH 3.0, 3.5., 4.0 and 4.5. The mixtures were then stored in the cold for several hours. After equilibration, the supernatant solutions were examined for unadsorbed protein. Calculations indicated the following amounts of Lactase LP had been adsorbed on the CM-cellulose media.

TABLE IV

| Sample | pH | LP Lactase Immobilized |
|---|---|---|
| 1 | 3.0 | 67.0% |
| 2 | 3.5 | 85.2% |
| 3 | 4.0 | 71.3% |
| 4 | 4.5 | 51.1% |

The immobilized CM-C lactase (pH 3.5) was used in further trials for the continuous hydrolysis of lactose.

The 12.0 grams of wet CM-C lactase complex was loaded into a Pharmacia K9/30 column to a bed height of 28 cm. Acetate buffer (0.05M, pH 3.5) at 40° C. was passed through the column until the washings were clear and indicated no detectable enzyme activity was present in the wash buffer. A substrate solution (10% crude lactose and including whey salts) was then flowed through the column at a flow rate of 60 milliliters per hour under continuous conditions. The lactose was at least 80 percent hydrolyzed by the enzymatic treatment. The enzymatic activity of the column was assayed by determining the degree of hydrolysis of the lactose in the effluent on a daily basis. After 10 days of continuous operation, it was determined from linear regression data that the bioreactor activity was gradually declining. The half-life lactase activity of the column was found to be 31 days. Half-life is the point where the bound enzyme had declined to one-half its original activity from the first day of operation.

The preparation of a CM-cellulose-tea polyphenol-lactase bioreactor system is described in the following example.

EXAMPLE II

Twelve grams of wet, preconditioned carboxymethyl cellulose prepared as described in Example I was stirred in 20 ml of distilled water to which 3 ml of 5% instant tea (Nestles 100% Tea) was added. The solution was stirred for 30 minutes and drained. The resulting carboxymethyl cellulose adduct, or tea polyphenol complex, was then washed with 3 volumes of acetate buffer, 0.05M, pH 3.5 and packed into a Pharmacia K9/30 column. 400 milliliters of acetate buffer was passed through the column at 4.0 ml/hr to remove any excess tea polyphenols.

A solution of lactase LP enzyme as described in Example I containing 300 milligrams of the enzyme in 150 of acetate buffer was then passed 3 times through the column at a flow rate of 2.0 milliliters per minute. From differential optical density measurements ($A_{260}/A_{230}$) of the enzyme solution, it was established that 27.4 milligrams of protein per gram of support had been adsorbed and cross-linked. The column was again washed with acetate buffer (0.05 M, pH 3.5) until no enzyme activity could be detected in the buffer wash. The column was then placed in continuous operation by flowing substrate solution (10% crude lactose) at 4.0 milliliters per minute, 45° C. for 27 days. The lactose is at least 80 percent hydrolyzed by the enzymatic treatment. Lactase activity of the bioreactor was established daily (Wallerstein lactase assay) and the data recorded. Linear regression analyses projected a half-life of 107 days for ths column. These data demonstrate that the tea polyphenol crosslinking procedure provided a more stable enzyme complex with a three-fold improvement in half-life functionality.

Accordingly, it will be recognized that in accordance with the present disclosure, immobilized enzyme compositions, and methods for preparing such compositions have been provided which have significant utility in processes for enzymatic treatment of food products. While various aspects of the invention have been particularly described with respect to specific enzyme and substrate materials, it will be appreciated that a broad range of enzyme-substrate systems and processes and other adaptations will be apparent from the present disclosure, and are intended to be within the scope of the present invention as defined by the following claims.

Various of the features of the invention are set forth in the following claims.

What is claimed is:

1. A method for preparing an immobilized enzyme composition comprising the steps of providing an enzyme composition to be immobilized, providing a suitable insoluble immobilization support for the enzyme, and combining said enzyme and said support with an edible water soluble tea polyphenol immobilization agent selected from the group consisting of green tea extract of *Camellia sinensis,* black tea extract of *Camellia sinensis,* (−) epi-gallocatechin gallate, (−) epi-catechingallate, (−) epi-gallocatechin, (−) epi-catechin, theogallin, *Camellia sinensis* tea flavanols, *Camellia sinensis* bisflavanols, *Camellia sinensis* tea flavanol oxidation polymers and mixtures thereof to form an immobilized enzymatically active composition comprising an adduct of said enzyme, said support and said tea polyphenol immobilization agent.

2. A method in accordance with claim 1 comprising the steps of forming an aqueous solution of said enyzme, forming a solution of the tea polyphenol immobilization agent, admixing said insoluble immobilization support with said tea polyphenol solution to form a tea polyphenol-support adduct and admixing said tea polyphenol-support adduct with said aqueous solution of said enzyme to provide a tea polyphenol-support-enzyme adduct.

3. A method in accordance with claim 1 wherein said support is an organopolymer having pendant carboxylic acid groups and wherein said enzyme is lactase.

4. A method in accordance with claim 3 wherein said support is carboxymethyl cellulose.

5. An immmobilized enzymatically active adduct comprising an enzyme, an immobilization support and an edible water soluble tea polyphenol immobilization agent.

6. The adduct of claim 5 wherein said immobilization support is an inorganic or organic support.

7. A composition in accordance with claim 5 wherein said support is an organopolymer having pendant carboxylic acid groups.

8. A composition in accordance with claim 6 wherein said support is in bead form.

9. A method for enzymatically processing of food products comprising the steps of providing an aqueous fluid dispersion of the food product to be processed which contains a reactant subject to enzymatic treatment, providing an insolubized enzyme composition comprising an insoluble support and an adduct of an edible water soluble tea polyphenol with an enyzme which is interactive with said reactant, contacting said aqueous dispersion of the food product with said insolubilized enzyme composition to enzymatically modify the food product, and separating the modified food product from the insolubilized enzyme composition.

10. A method in accordance with claim 9 wherein said enzyme composition is a tea polyphenollactase adduct and wherein said aqueous food product dispersion is a diary derived fluid containing lactose, and wherein said dairy fluid is contacted with said enzyme composition for a sufficient period of time to hydrolyze at least 80 weight percent of said lactose to glucose and galactose.

* * * * *